United States Patent [19]

Jotterand

[11] 4,092,329
[45] May 30, 1978

[54] PROCESS FOR THE SYNTHESIS OF CERTAIN 2-AMINO-5-CYANOTHIOPHENES

[75] Inventor: Armand Jotterand, Dornach, SO, Switzerland

[73] Assignee: Sandoz Ltd., Basel, Switzerland

[21] Appl. No.: 597,003

[22] Filed: Jul. 18, 1975

Related U.S. Application Data

[62] Division of Ser. No. 420,223, Nov. 29, 1973, abandoned.

[30] Foreign Application Priority Data

Dec. 1, 1972 Switzerland ............... 17535/72
Dec. 12, 1972 Switzerland ............... 18199/72

[51] Int. Cl.² .............. C07D 333/36; C07D 333/38; C07D 333/42
[52] U.S. Cl. ............ 260/329 AM; 260/329 S; 260/332.2 C; 260/332.3 R; 260/332.5
[58] Field of Search ......... 260/329 AM, 332.8, 329 S, 260/332.2 C, 332.3 R, 332.5

[56] References Cited

U.S. PATENT DOCUMENTS 2,570,083  10/1951  Wadley ........................... 260/332.8

*Primary Examiner*—James O. Thomas, Jr.
*Assistant Examiner*—R. A. Siegel
*Attorney, Agent, or Firm*—Gerald D. Sharkin; Richard E. Vila; Melvyn M. Kassenoff

[57] ABSTRACT

The invention relates to a process which comprises reacting a compound of formula I,

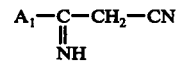

I in which $A_1$ is a radical which does not compete with the activity of the

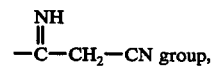 group, or a tautomer thereof,
with a compound of formula II, $$A_2 - CH_2 - CN$$　　　　II in which $A_2$ is a radical which does not compete with the activity of the —CH$_2$CN group of the compound of formula II but provides the vicinal methylene group with sufficient acidity to react with the =NH group of the compound of formula I,
and with sulphur,
to obtain a compound of formula III,

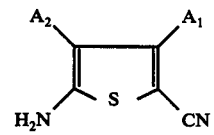

III in which $A_1$ and $A_2$ are as defined above, which compounds of formula III are useful as intermediates for the production of dyestuffs.

18 Claims, No Drawings

PROCESS FOR THE SYNTHESIS OF CERTAIN 2-AMINO-5-CYANOTHIOPHENES

This application is a division of application Ser. No. 420,223, filed on Nov. 29, 1973 and now abandoned.

The invention relates to a process for the production of thiophene compounds.

More particularly, the invention relates to a process which comprises reacting a compound of formula I,

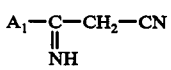

in which $A_1$ is a radical which does not compete with the activity of the

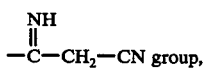

or a tautomer thereof,
with a compound of formula II, $$A_2 - CH_2 - CN \qquad II$$

in which $A_2$ is a radical which does not compete with the activity of the —CH$_2$CN group of the compound of formula II but provides the vicinal methylene group with sufficient acidity to react with the =NH group of the
compound of formula I,
and with sulphur,
to obtain a compound of formula III,

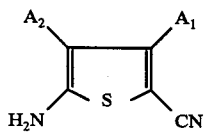

in which $A_1$ and $A_2$ are as defined above.

The reaction of a compound of formula I with a compound of formula II, and with sulphur is conveniently carried out using approximately stoichiometric amounts of the reactants. The reaction is suitably carried out in an inert organic medium; suitable solvents are those which boil at 80° C or higher under standard pressure, for example, ethanol, dioxene, toluene, benzene, chlorobenzene, dichloroethane and tetrachloroethane. The reaction may be carried out in the presence of a basic catalyst, e.g., tertiary amines such as triethylamine.

In general, the reaction is exothermic and can be started at room temperature. Conveniently, the reaction mixture is maintained at a temperature of at least 50° C, preferably between 80° and the boiling point, e.g., reflux temperature. The reaction times will vary, depending on other reaction conditions, e.g., temperature and solvents; however, in general, satisfactory results are obtained with reaction times in the range of from 1 to 20 hours.

On conclusion of the reaction, the product may be isolated by conventional methods, e.g., by filtration, and if necessary by subsequent washing and/or recrystallization.

As examples of suitable $A_1$ radicals may be given alkyl radicals and unsubstituted and substituted phenyl radicals. The alkyl radicals preferably contain 1 to 8, more preferably 1 to 3, carbon atoms, e.g., methyl, ethyl, propyl and iso-propyl, with methyl being most preferred.

When $A_1$ is a substituted phenyl radical, its substituents are selected from the group consisting of halogen, ($C_{1-3}$) alkyl, cyano and nitro. By halogen is to be understood fluorine, chlorine or bromine, with chlorine being preferred.

Preferably, when $A_1$ signifies a phenyl radical such phenyl radical is unsubstituted or bears 1 or 2 substituents. As examples of suitable $A_1$ substituted phenyl radicals may be given o or p-nitrophenyl, p-cyanophenyl, p-chlorophenyl, 2,5-dichlorophenyl and 4-chloro-5-methylphenyl.

The most preferred $A_1$ substituent is methyl.

As examples of suitable $A_2$ radicals may be given substituted phenyl radicals which bear at least one substituent selected from the group consisting of nitro, cyano and alkylsulphonyl in positions ortho and/or para to the cyanomethyl group, which substituted phenyl radicals may also bear an alkyl radical and/or halogen atom; cyano; unsubstituted and substituted alkoxycarbonyl, aryloxycarbonyl, carbamoyl, thiocarbamoyl, alkylcarbonyl and benzoyl radicals; and alkoxy and phenoxy radicals. Representative significances of $A_2$ are those wherein $A_2$ is other than a substituted or unsubstituted thiocarbamoyl radical.

Preferably, substituted phenyl radicals, as $A_2$, bear one alkylsulphonyl group, one or two nitro groups, one or two cyano groups or one cyano and one nitro group, which group or groups are located in positions ortho and/or para to the cyanomethyl group. In addition, the such substituted $A_2$ phenyl radicals may bear an alkyl group of 1 to 3 carbon atoms, e.g., methyl, ethyl, propyl or iso-propyl, preferably methyl, or a halogen atom, e.g., chlorine, bromine or fluorine, preferably chlorine. The alkylsulphonyl group preferably contains 1 to 3 carbon atoms, e.g., methyl-, ethyl-, propyl- or iso-propylsulphonyl, preferably methylsulphonyl. Thus, specific examples of $A_2$ substituted phenyl radicals include p-cyanophenyl, p-nitrophenyl, p-methylsulphonylphenyl, o-nitrophenyl, 2-nitro-4-methylphenyl and 2-chloro-4-nitrophenyl.

The unsubstituted and substituted carbamoyl, thiocarbamoyl, alkoxycarbonyl, alkylcarbonyl and benzoyl radicals may be represented by the following formulae:

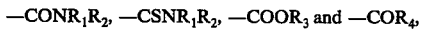

in which
  $R_1$ signifies a hydrogen, an unsubstituted ($C_{1-8}$) alkyl radical or a ($C_{1-8}$) alkyl radical substituted by a hydroxy group or by a phenyl radical; an unsubstituted phenyl radical; an unsubstituted cycloalkyl radical of 5 to 7 ring carbon atoms, preferably cyclohexyl; or a phenyl radical substituted by up to three substituents selected from the group consisting of chlorine atoms and ($C_{1-3}$) alkyl groups,
  $R_2$ signifies a hydrogen atom, an unsubstituted ($C_{1-8}$) alkyl radical or a ($C_{1-8}$) alkyl radical substituted by a hydroxy group,
  $R_3$ signifies an unsubstituted ($C_{1-8}$) alkyl radical; a cycloalkyl radical of 5 to 7 ring carbon atoms, preferably cyclohexyl; a ($C_{1-8}$) alkyl radical substituted by a hydroxy or cyano group, a chlorine, bromine or fluorine, preferably chlorine, atom, or by a phenyl radical; unsubstituted phenyl radical; or a phenyl radical substituted by methyl or ethyl, and $R_4$ signifies an unsubstituted ($C_{1-8}$) alkyl radical; a ($C_{1-8}$) alkyl radical substituted by a hydroxy or cyano group or by a chlorine, bromine or fluorine, preferably chlorine, atom; an unsubstituted phenyl radical or a phenyl radical substituted by methyl or ethyl.

Preferably, where any one of $R_1$ to $R_4$ signifies an alkyl radical, such alkyl radical contains 1 to 6, more preferably 1 to 4, carbon atoms.

As examples of substituted carbamoyl and thiocarbamoyl radicals may be given those derived from the following amines: methylamine, ethylamine, propylamine, isopropylamine, ethanolamine, isopropanolamine, aniline, toluidine, xylidene, benzylamine, dimethylamine, diethylamine, diethanolamine, di-isopropanolamine, N-methylaniline N-ethylaniline, N-methyltoluidine, N-ethyltoluidine, mesidine and cyclohexylamine, the lower unsubstituted mono- and dialkylamines being preferred, the unsubstituted carbamoyl and thiocarbamoyl groups (—$CONH_2$ and '$CSNH_2$) being more preferred.

As examples of $R_3$ may be given methyl, ethyl, propyl, isopropyl, n-butyl, tert. butyl, cyclohexyl, hydroxyethyl, β-chloroethyl, β-cyanoethyl, β- or γ-hydroxypropyl, benzyl and phenylethyl. Preferred $R_3$ radicals are the unsubstituted lower alkyl radicals. Especially preferred are methyl and ethyl.

As examples of $R_4$ radicals may be given those mentioned above for $R_3$ with the exception of the phenyl-substituted alkyl radicals. A particularly preferred $R_4$ radical is unsubstituted phenyl.

Preferred significances of $A_2$ are the phenyl radicals substituted as stated hereinbefore, the radicals —$COR_4$, —$COOR_3$, —$CONR_1R_2$, —$CSNR_1R_2$ as defined above and —CN, with —$CUR_4$, —$COOR_3$, —$CONR_1R_2$, —$CSNR_1R_2$ and —CN being more preferred.

More preferred significances for $A_2$ are —CN, —$CONH_2$, —$CSNH_2$ and —$COOR_3'$, in which $R_3'$ signifies an unsubstituted ($C_{1-4}$) alkyl radical, preferably methyl or ethyl, with the cyano radical being most preferred.

Preferably, $A_1$ is $C_{1-8}$alkyl, phenyl or phenyl substituted by 1 or 2 substituents selected from the group consisting of halo, $C_{1-3}$alkyl, cyano and nitro, and $A_2$ is phenyl having an ortho or para $C_{1-3}$alkylsulfonyl group or one or two nitro groups, one or two cyano groups or one nitro and one cyano group each of hich is in an ortho or para position, which substituted phenyl group is further unsubstituted or further substituted by $C_{1-3}$alkyl or halo; cyano; $C_{1-4}$alkoxy; phenoxy; —$CONR_1R_2$; —$CSNR_1R_2$; —$COOR_3$ or —$COR_4$, wherein $R_1$, $R_2$, $R_3$ and $R_4$ are as defined above.

The compounds of formula III are useful as intermediates for the production of dyestuffs. For example, the compounds of formula III can be converted into useful azo dyes by diazotization and coupling with a coupling component such as N,N-diethylaniline or its 3-acetamido derivative in conventional manner. The resulting final compounds can be used in the dyeing of textiles, e.g., polyesters, in conventional manner. In particular, those compounds of formula III wherein $A_1$ is alkyl or an unsubstituted or substituted phenyl radical and $A_2$ is —CN, —$COOR_3$ or —$COR_4$ as hereinbefore defined are useful in the production of dyes as disclosed in application Ser. No. 375,436, filed Jul. 2, 1973 and now abandoned.

The compounds of formula III',

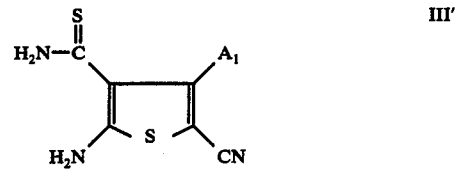

in which $A_1$ is as defined above, are useful as intermediates in the production of 4-amino-6-cyano-thieno-[2,3-c]-thiazolenes of the type disclosed in German Offenlegungsschrift No. 2,101,701.

The compounds of formula III', as defined above, may also be produced by reacting a compound of formula III",

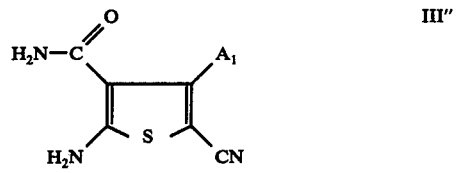

with phosphorus pentasulphide according to known methods [c.f. Latvijas PSR Zinatnu., Akad. Vestri. Kim. Ser. 1963 (4) 469–477 and C.A. 60, 5391.]

The compounds of formulae III''' and III$^{IV}$,

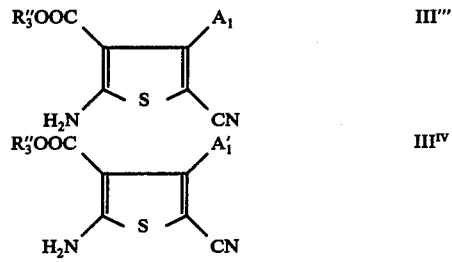

in which $A_1$ is as defined above,
$R_3''$ signifies an alkyl radical of 1 to 4 carbon atoms, and
A' is methyl or unsubstituted or substituted phenyl, may be saponified and decarboxylated as described by K. Gewald, Z. Chem. 7 (5) 186 (1967) to form compounds of formulae VII and VIII, respectively,

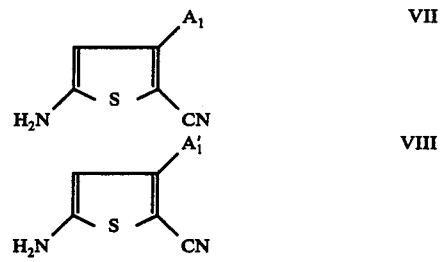

which compounds are useful as intermediates in the production of dyes as disclosed in application Ser. No. 375,425, filed July 2, 1973, and now abandoned.

The compounds of formula I and II are known or may be produced according to known methods.

The following Examples serve to further illustrate the present invention. In the Examples all parts and percentages are by weight unless otherwise stated. The parts by weight relate to the parts by volume as grams to milliliters. The temperatures are in degrees centigrade.

EXAMPLE 1

A reactor vessel holding 350 parts by volume and equipped with a reflux condenser is loaded with 82 parts of the compound of formula XI,

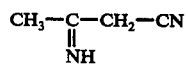           XI 66 parts malononitrile, 32 parts sulphur and 140 parts by volume of ethanol. The mixture is stirred into suspension and heated. At 50°–60° the reaction becomes noticeably exothermal and the temperature rises rapidly to 90°–100°. The heat of the reaction is controlled so as to maintain normal reflux for 2 hours. The reaction mixture thickens and takes on a dark brown color. On cooling, the reaction product is filtered and washed with 150 parts by volume of ethanol. The presscake is dried at 60° under vacuum. After recrystallization from ethanol, a product is obtained in 65% yield, with a melting point of 220°–222°. It is of formula XII,

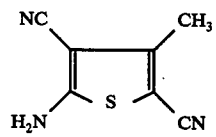           XII

The following values were obtained by elementary analysis:

|  | C | H | N | S |
|---|---|---|---|---|
| Calculated: | 51.6 | 3.1 | 25.8 | 19.6 |
| Found: | 51.5 | 3.2 | 25.8 | 19.6 |

EXAMPLE 2

Using the same procedure as Example 1, except that the 66 parts malononitrile are replaced by the corresponding amount of cyanoacetic acid ethyl ester, the compound of formula XIII,

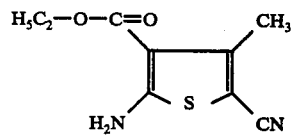           XIII is obtained in 70% yield after recrystallization from ethanol/dioxane, with a melting point of 200°–202°.

EXAMPLE 3

Using the procedure as described in Example 1, except that the 66 parts malononitrile are replaced by the corresponding amount of cyanoacetic acid methyl ester, the compound of formula XIV,

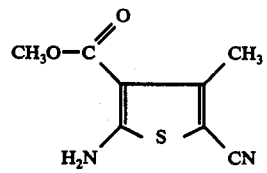           XIV is obtained in 80% yield.

EXAMPLE 4

Using the same procedure as Example 1, except that the 82 parts of the compound of formula XI are replaced by the corresponding amount of β-imino-β-phenylpropionic acid nitrile, the compound of formula XV,

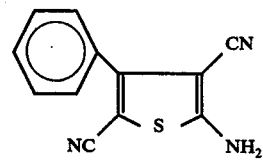           XV is obtained in 60 % yield, having a melting point of 230° to 237° after recrystallization from ethanol/dioxane. The reaction is not so exothermic as that of Example 1 and the temperature is maintained between 90° and 100° with heating.

The followng values were obtained by elementary analysis:

|  | C | H | N | S |
|---|---|---|---|---|
| Calculated: | 64.0 | 3.1 | 18.7 | 14.2 |
| Found: | 64.2 | 3.4 | 18.6 | 14.3 |

EXAMPLE 5

Employing the procedure of Example 1, but replacing the 66 parts of malonitrile with the corresponding amount of cyanoacetamide, the compound of formula XVI,

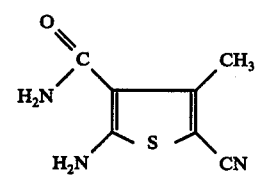           XVI is obtained in 55% yield with a melting point of 235°–237° after recrystallization from ethanol/dioxane. The reaction is not strongly exothermic and reflux temperature is maintained by heating.

The following values were obtained by elementary analysis:

|  | C | H | N | O | S |
|---|---|---|---|---|---|
| Calculated: | 46.4 | 3.9 | 23.2 | 8.8 | 17.7 |
| Found: | 46.5 | 3.9 | 23.0 | 9.0 | 17.8 |

The following compounds may be prepared in a manner analogous to the above Examples.

EXAMPLE 6

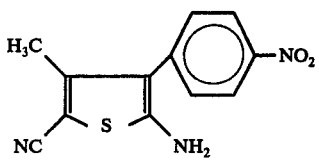

EXAMPLE 7

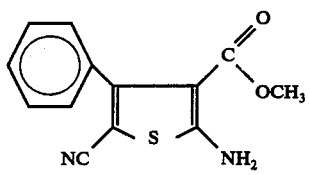

EXAMPLE 8

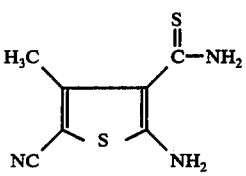

EXAMPLE 9

A reaction vessel holding 2500 parts by volume and fitted with a reflux condenser is loaded with 196 parts 2-amino-3-methoxycarbamyl-5-cyano-3-methylthiophene in 400 parts of a 20% potash lye in water and ethanol (ethanol to water ratio 1:1). The mixture was stirred and heated to reflux temperature. After 3 hours, the mixture was cooled, mixed with 800 parts water and acidified with dilute sulphuric acid. The light brown crude product was scrubbed and washed with water. The filter cake was dried at 60° in vacuum. After recrystallization from dimethylformamide, the product of the formula

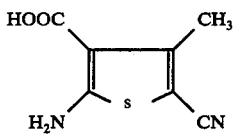

was obtained having a melting point of 165° to 167°. By decarboxylation according to conventional methods, the product of the formula

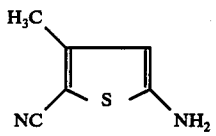

was obtained having a melting point of 71° to 73°.

What I claim is:

1. A process for the synthesis of a compound of the formula

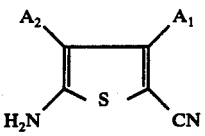

comprising reacting a compound of the formula

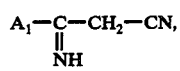

or a tautomer thereof, with a compound of the formula

and with sulfur, in an inert organic medium and at a reaction temperature ranging from room temperature to the boiling point of the reaction mixture, whereby a compound of the formula

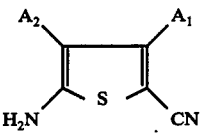

is obtained, wherein
$A_1$ is $C_{1-8}$alkyl, phenyl or phenyl substituted by 1 or 2 substituents each of which is independently halo, $C_{1-3}$alkyl, cyano or nitro, and $A_2$ is 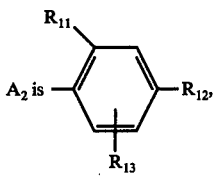

cyano, $C_{1-4}$alkoxy, phenoxy, —$CONR_1R_2$, —$CSNR_1R_2$, —$COOR_3$ or —$COR_4$, wherein
  $R_1$ is hydrogen; $C_{1-8}$alkyl; $C_{1-8}$alkyl substituted by hydroxy or phenyl; $C_{5-7}$cycloalkyl; phenyl or phenyl substituted by 1 to 3 substituents each of which is independently chloro or $C_{1-3}$alkyl,
  $R_2$ is hydrogen, $C_{1-8}$alkyl or $C_{1-8}$-hydroxyalkyl,
  $R_3$ is $C_{1-8}$alkyl; $C_{5-7}$cycloalkyl; $C_{1-8}$alkyl substituted by hydroxy, cyano, chloro, bromo, fluoro or phenyl; phenyl or phenyl substituted by methyl or ethyl,
  $R_4$ is $C_{1-8}$alkyl; $C_{1-8}$alkyl substituted by hydroxy, cyano, chloro, bromo or fluoro; phenyl or phenyl substituted by methyl or ethyl,
  $R_{11}$ is hydrogen, $C_{1-3}$alkylsulfonyl, nitro or cyano,
  $R_{12}$ is hydrogen, $C_{1-3}$alkylsulfonyl, nitro, cyano, $C_{1-3}$alkyl or halo, and
  $R_{13}$ is hydrogen, $C_{1-3}$alkyl or halo, with the provisos that
    (a) at least one of $R_{11}$ and $R_{12}$ is $C_{1-3}$alkylsulfonyl, nitro or cyano,
    (b) when one of $R_{11}$ and $R_{12}$ is $C_{1-3}$alkylsulfonyl, the other is other than $C_{1-3}$alkylsulfonyl, nitro or cyano, and
    (c) $R_{13}$ is hydrogen when $R_{12}$ is $C_{1-3}$alkyl or halo.

2. A process according to claim 1 wherein said inert organic medium has a boiling point of at least 80° C.

3. A process according to claim 1 wherein the reaction temperature ranges from 50° C. to the boiling point of the reaction mixture.

4. A process according to claim 3 wherein the reaction temperature ranges from 80° C. to the boiling point of the reaction mixture.

5. A process according to claim 3 wherein approximately stoichiometric amounts of the three reactants are employed.

6. A process according to claim 1 wherein approximately stoichiometric amounts of the three reactants are employed.

7. A process according to claim 1 wherein
$R_1$ is hydrogen; $C_{1-4}$alkyl; $C_{1-4}$alkyl substituted by hydroxy or phenyl; $C_{5-7}$cycloalkyl; phenyl or phenyl substituted by 1 to 3 substituents each of which is independently chloro or $C_{1-3}$-alkyl,
$R_2$ is hydrogen, $C_{1-4}$alkyl or $C_{1-4}$hydroxyalkyl,
$R_3$ is $C_{1-4}$alkyl; $C_{5-7}$cycloalkyl; $C_{1-4}$alkyl substituted by hydroxy, cyano, chloro, bromo, fluoro or phenyl; phenyl or phenyl substituted by methyl or ethyl, and
$R_4$ is $C_{1-4}$alkyl; $C_{1-4}$alkyl substituted by hydroxy, cyano, chloro, bromo or fluoro; phenyl or phenyl substituted by methyl or ethyl.

8. A process according to claim 7 wherein

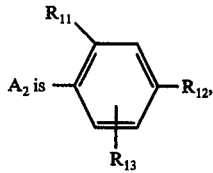

cyano, $-CONR_1R_2$, $-CSNR_1R_2$, $-COOR_3$ or $-COR_4$.

9. A process according to claim 8 wherein
$A_2$ is cyano, $-CONR_1R_2$, $-CSNR_1R_2$, $-COOR_3$ or $-COR_4$.

10. A process according to claim 9 wherein
$A_2$ is cyano, $-CONH_2$, $-CSNH_2$ or $-COOR_3'$, wherein
$R_3'$ is $C_{1-4}$alkyl.

11. A process according to claim 10 wherein
$R_3'$ is methyl or ethyl.

12. A process according to claim 1 wherein
$A_1$ is $C_{1-3}$alkyl, phenyl or phenyl substituted by 1 or 2 substitutents each of which is independently halo, $C_{1-3}$alkyl, cyano or nitro.

13. A process according to claim 12 wherein
$A_1$ is methyl, phenyl or phenyl substituted by 1 or 2 substituents each of which is independently halo, $C_{1-3}$alkyl, cyano or nitro.

14. A process according to claim 1 wherein

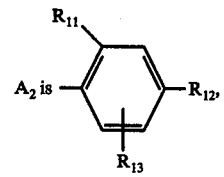

cyano, $C_{1-4}$alkoxy, phenoxy, $-CONR_1R_2$, $-COOR_3$ or $-COR_4$.

15. A process according to claim 14 wherein
$A_1$ is methyl, and
$A_2$ is cyano.

16. A process according to claim 14 wherein
$A_1$ is methyl, and
$A_2$ is ethoxycarbonyl.

17. A process according to claim 14 wherein
$A_1$ is methyl, and
$A_2$ is methoxycarbonyl.

18. A process according to claim 14 wherein
$A_1$ is phenyl, and
$A_2$ is cyano.

* * * * *